US005540678A

United States Patent [19]
Long et al.

[11] Patent Number: 5,540,678
[45] Date of Patent: Jul. 30, 1996

[54] APPARATUS AND METHOD FOR EFFICIENTLY TRANSMITTING OPTIC ENERGY FROM A REUSEABLE OPTIC ELEMENT TO A DISPOSABLE OPTIC ELEMENT

[75] Inventors: Gary Long; Craig Davis, both of Cincinnati, Ohio; Richard L. Studer, Villa Hills, Ky.

[73] Assignee: Laser Centers of America, Cincinnati, Ohio

[21] Appl. No.: 264,360

[22] Filed: Jun. 22, 1994

Related U.S. Application Data

[63] Continuation of Ser. No. 999,321, Dec. 31, 1992, abandoned.

[51] Int. Cl.$^6$ ............................................. A61B 17/36
[52] U.S. Cl. .................. 606/10; 128/898; 606/17; 385/39
[58] Field of Search ...................... 606/10–12, 15–18; 385/27, 31–35, 39, 50; 128/898

[56] References Cited

U.S. PATENT DOCUMENTS 4,431,262  2/1984  Tolles ........................ 385/147
4,728,169  3/1988  Campbell et al. ............... 385/32
4,785,805  11/1988  Joffe et al. .
4,895,145  1/1990  Joffe et al. .
5,029,957  7/1991  Hood ............................ 385/27

*Primary Examiner*—Angela D. Sykes
*Assistant Examiner*—Michael Peffley
*Attorney, Agent, or Firm*—Lowe, Price, LeBlanc & Becker

[57] ABSTRACT

Apparatus and method are provided to ensure efficient transmission of a light flux from a first optic element to a second optic element located close to but not in intimate contact therewith. This is accomplished by providing an intermediate element made of a light-transmissive conformable material which is disposed so as to be simultaneously pressed to both a light-transmitting surface of one element and a light-receiving surface of the second element. Selection of a suitable material for the conformable element ensures the desired optical transmissibility and intimate contact, and thereby significantly reduces Fresnel and other losses of the type normally encountered when two relatively hard optic elements cannot be placed in intimate contact with each other. Commercially available two-component silicone rubber materials are found to be suitable for forming the light-transmissive conformable optic element.

21 Claims, 5 Drawing Sheets

U.S. Patent    Jul. 30, 1996    Sheet 1 of 5    5,540,678
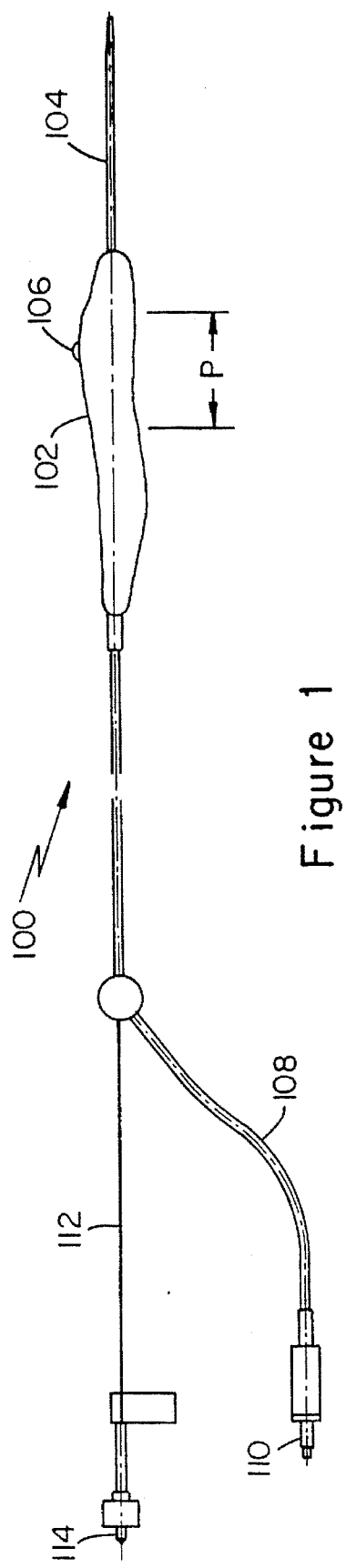
Figure 1
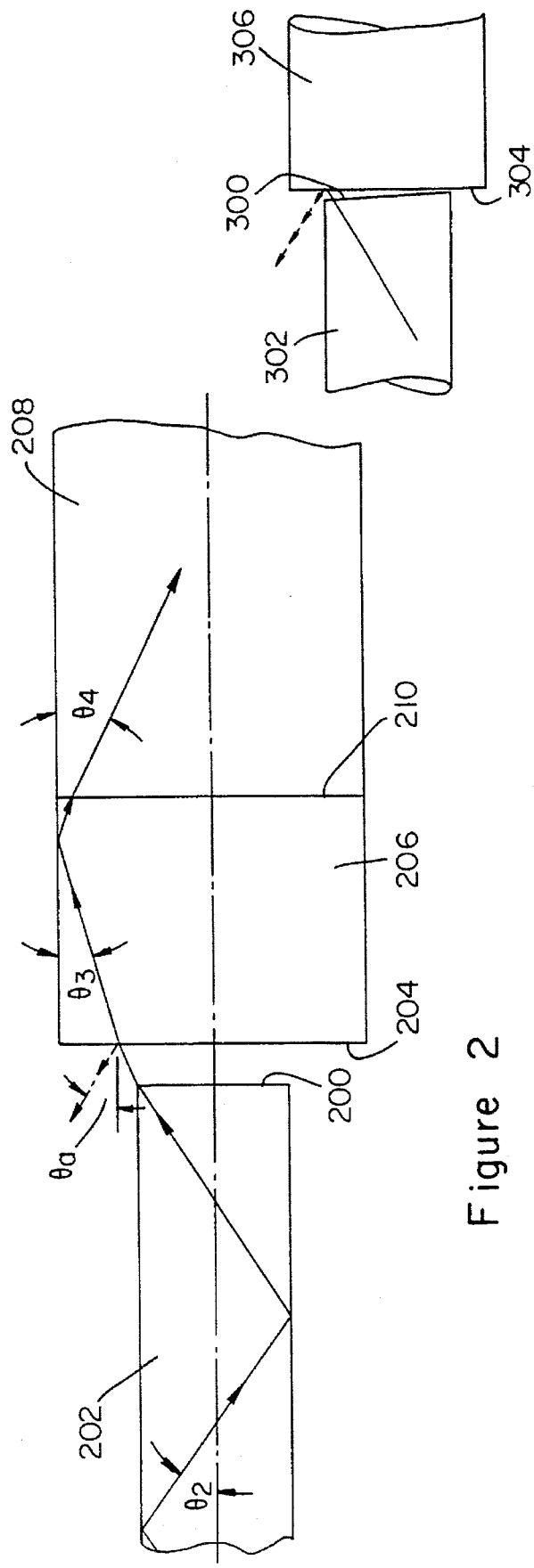
Figure 3
Figure 2

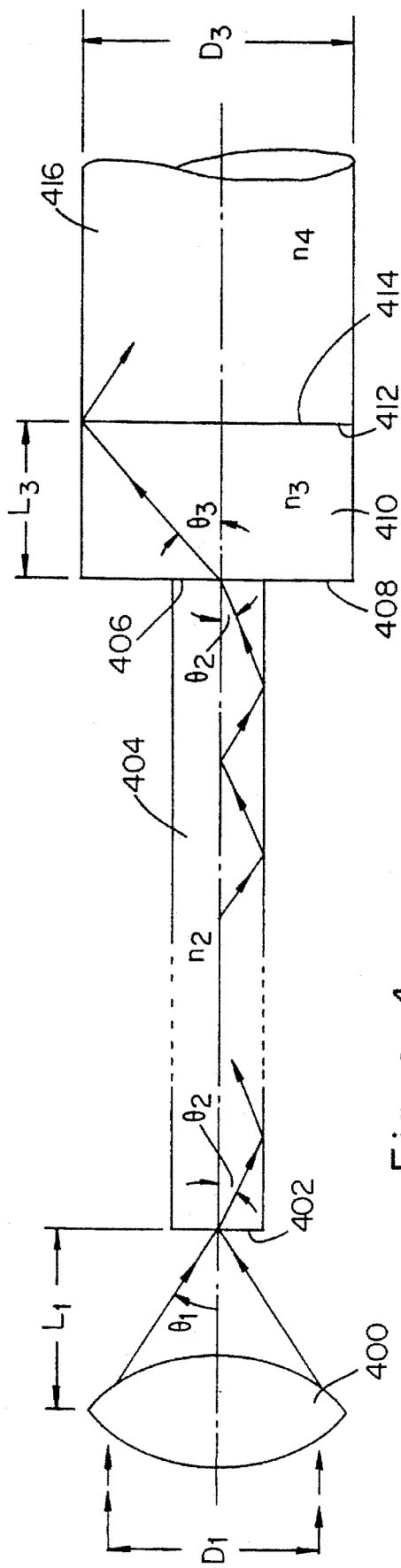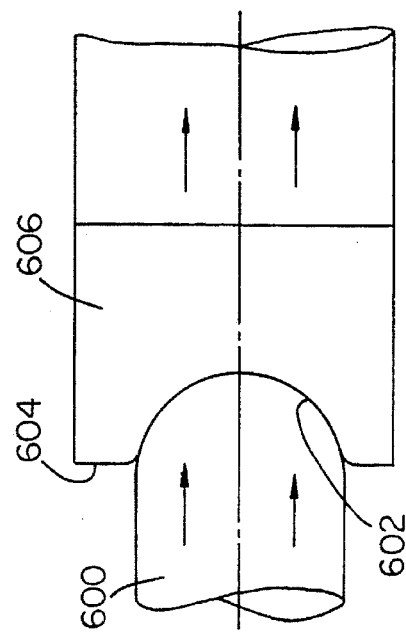
Figure 4
Figure 5
Figure 6

APPARATUS AND METHOD FOR EFFICIENTLY TRANSMITTING OPTIC ENERGY FROM A REUSEABLE OPTIC ELEMENT TO A DISPOSABLE OPTIC ELEMENT

This application is a continuation of application Ser. No. 07/999,321 filed Dec. 31, 1992, now abandoned.

FIELD OF THE INVENTION

This invention relates to apparatus and a method for efficiently transmitting optic energy from one optic element to another optic element, and more particularly to the provision of an efficient optical interface including an optically transmissive conformable element between a long-use optic element and a disposable optic element temporarily utilized therewith.

BACKGROUND OF THE PRIOR ART

A variety of applications require the provision of an optic energy flux between cooperating optic elements, e.g., between two optic fibers or from a relatively expensive long-use optic element such as an optic fiber into a disposable end-use element which may become damaged or contaminated during use. One example of the latter type of use is a laser surgical system in which the surgeon holds a slim elongate tool connected via an optic fiber to a laser energy source. The surgical tool is usually formed to utilize a controlled flux of laser energy at a surgical tip element.

As the surgeon employs the tip element, either to radiate laser energy to vaporize tissue and thereby perform incisions, or to apply a heated portion of the tip element to cauterize tissue or to coagulate body fluids, the material of the tip element is subjected to severe thermal cycling. In addition, due to carbonization of heated body tissue on its surface, the efficiency of the surgical tip may be reduced over time. When damage to or deterioration of the tip element becomes unacceptable, or as different types of tissue are encountered during surgery, the surgeon may want to replace the tip element.

If the tip element were integrated with the optic fiber connected to the laser energy source its replacement would be very expensive and could be time-consuming and tedious. It is therefore desirable to provide a disposable laser energy delivering tip element assembly which can be quickly and efficiently coupled optically to a long-use optic fiber end that is protected within the hand-held surgical tool. Such a facility would also allow a surgeon to simply replace one tip element/assembly with another, e.g., to operate on a different patient, quickly and easily. Similarly, the surgeon may selectively use a succession of differently shaped and sized tip elements as he or she encounters different types of tissues and needs in operating on a single patient.

A variety of laser surgical systems including disposable elements are known. These include, for example, those patented in U.S. Pat. Nos. 4,785,805 and 4,895,145, both to Joffe et al. These patents provide a two-component laser delivery system for surgical and endoscopic applications. The disclosed apparatus includes a reuseable head portion for insertion into a laser energy generating apparatus and a disposable optic guide portion engageable therewith. However, making the integrated system from the laser source onward disposable may be quite expensive and is preferably avoided. The problem, therefore, narrows down to how to efficiently couple the distal end of an optic fiber via a disposable and relatively inexpensive optical interface and thus to a tip element in such a way that transmission losses are minimized and tip elements readily replaced by a busy surgeon.

Although the preferred embodiment described below with reference to the accompanying drawing figures relates to a laser surgical application, it should be appreciated that the invention may be readily utilized in other applications. For example, an inspection system in a radioactive environment may include an optical fiber through which a flux of optical energy is sent in a forward direction and through which a portion of reflected optic energy is returned for analysis. Such a system may include a disposable end element exposed to radioactivity and therefore needing to be replaced periodically. Another example may be the use of optic observation and sensing elements disposed on space craft where there may be eventually eroded or otherwise damaged and may have to be replaced in space by astronauts operating under severe physical constraints. It is believed that the invention described below solves these and other comparable problems requiring efficient optical coupling between any two cooperating optic elements, and may be advantageously used to optically couple a long-use optic element and a cooperating replaceable element.

SUMMARY OF THE INVENTION

It is a principal object of the present invention to provide efficient optical coupling between two optic elements held in a cooperating relationship with each other.

It is another object of this invention to provide an inexpensive means to ensure efficient optical coupling between a long-use optic element and a replaceable optic element cooperating therewith during use.

It is yet another object of this invention to provide a system for enabling efficient transmission of an optic energy flux between a first optic element and a second optic element held in a cooperative relationship with respect to one another to provide respective portions of a common optic path between a source of the optic energy flux and the location at which the optic energy flux is utilized.

It is a related further object of this invention to provide a system for establishing efficient optical communication between an energy-emitting surface of a first optic element and an adjacently located but not directly contacting optic energy-receiving surface of a second optic element.

In another aspect of this invention there is provided a method for enabling efficient optic communication between two cooperating but not directly contacting optic elements.

It is a related further object of this invention to provide a method for simply, inexpensively and efficiently coupling a long-use optic element to a disposable optic element readily placed in a cooperating relationship therewith.

These and other objects, according to a preferred embodiment of this invention, are realized by providing a system for establishing efficient optical communication between a first optic element and a second optic element, the system comprising an optically transmissive conformable element for simultaneously and conformably contacting both an optic energy-emitting surface of the first element and an optic energy-receiving surface of the second element to provide an optic path therebetween, and means for maintaining the conformable element in said simultaneous conforming contact with both the first and second optic elements.

In a related aspect of this invention there is provided a method for enabling efficient optical communication between a first optic element having an optic energy-emitting surface in a predetermined disposition with respect to an optic energy-receiving surface of a second optic element, comprising the step of providing an optically transmissive conformable element in simultaneous and conforming contact with both said optic energy-emitting surface of the first element and the optic energy-receiving surface of the second optic element.

BRIEF DESCRIPTION OF THE DRAWING

FIG. 1 is a schematic view of a laser energy surgical system including a hand-held surgical tool connected at one end to an optic fiber and at another end to a laser energy-delivering tip element.

FIG. 2 is a diagram of exemplary optical paths traversed by an exemplary ray in a flux of optic energy between cooperating optic elements with only ambient air between a pair of adjacent substantially parallel optic energy-transmitting surfaces.

FIG. 3 is a side perspective view of two optic elements the light-transmitting end surfaces whereof are not in intimate contact with each other.

FIG. 4 is a diagram of optical paths travelled by an exemplary ray in a flux of optic energy received from a source and transmitted through an optic system comprising a lens, an optic fiber, an intermediate element, and another optic element.

FIG. 5 is a longitudinal cross-section of a set of cooperating optic elements including an optic fiber with a plane distal end surface in intimate contact with an intermediate conformable element.

FIG. 6 is a sectional view of cooperating optic elements including an optic fiber with a rounded light-transmitting distal end and an intermediate element conformably fitted thereto.

DETAILED DESCRIPTION OF THE PREFERRED EMBODIMENTS

Figure 7:
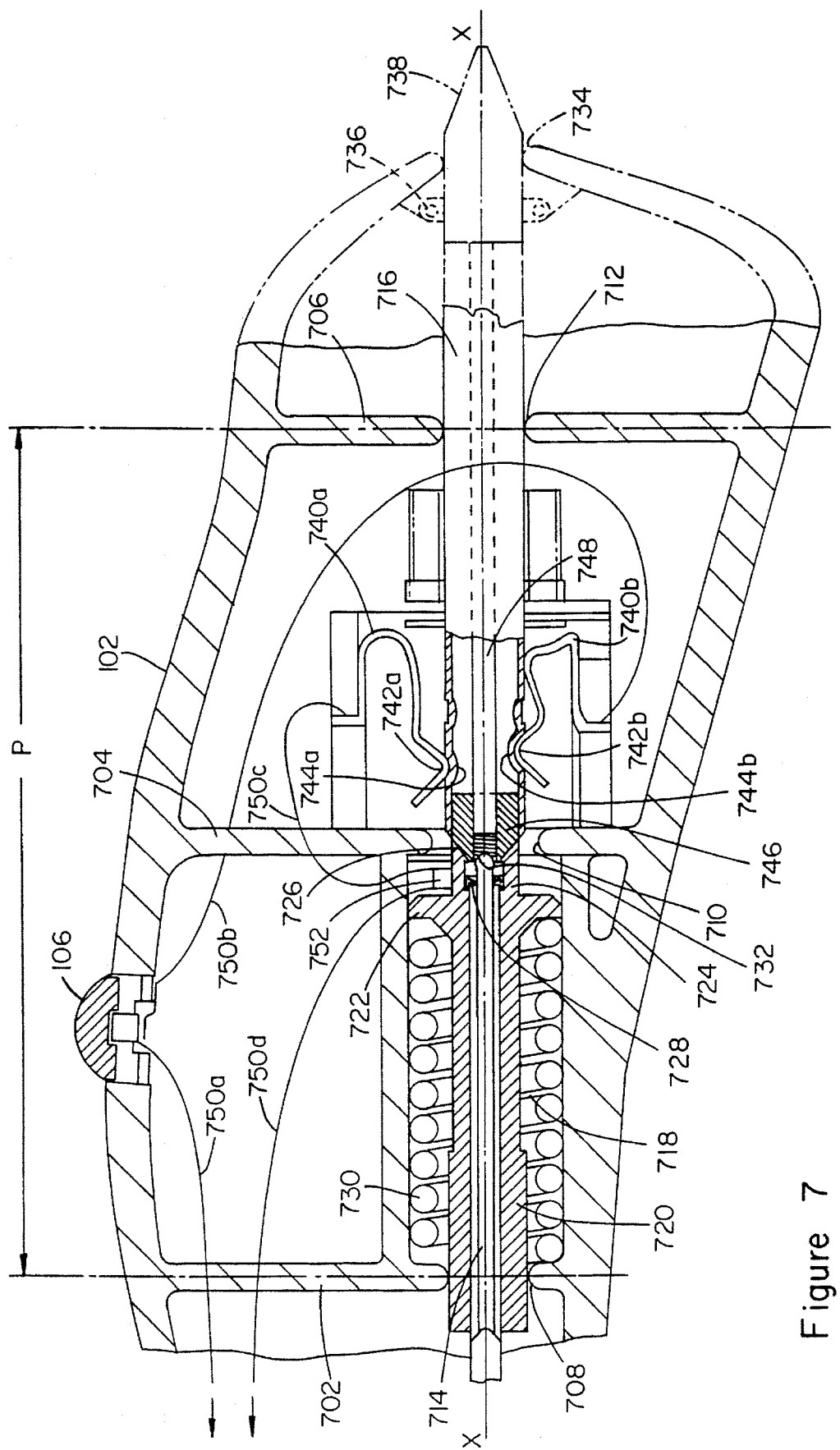
FIG. 7 is a partial longitudinal cross-sectional view of a hand-held laser surgical tool body, to explain the internal structure according to a preferred embodiment of this invention.

As noted earlier, many optical energy systems include cooperating optical elements with "light" transmitted from a light-emitting surface of one element to a light-receiving surface of another element. The term "light" as used herein is intended to mean electromagnetic radiation within a selected waveband. Such "light" may be infrared, visible, ultra-violet, X-ray, monochromatic or polychromatic, polarized, and incoherent or laser, depending on the particular application at hand. Regardless of the wavelength involved, it is always desirable to minimize transmission losses at interfaces between cooperating optic elements. The present invention is intended to minimize such losses and to enable efficient transmission of light between cooperating optic elements.

Important elements of an exemplary optical system, namely a laser surgical system, are best seen in FIG. 1. A surgeon employing such a laser surgical system 100 typically holds in his or her hand a lightweight elongate surgical tool body 102 having at a front end an extended tip assembly 104 which, depending on the surgical need, may employ emitted laser energy for surgery and/or to heat a tip surface for cauterization of incised blood vessels or for coagulation of body fluids.

The surgical tool body 102 has an ergonomically designed slim shape intended to fit comfortably to the surgeon's hand, and includes a pressure-actuated switch 106 by which the surgeon can control the applied energy flux. The exact location of switch 106 is a matter of design choice.

Laser energy is conveyed through an optical fiber protectively contained within a sheath 108 which is connected by a suitably designed fitting 110 at one end to a laser energy source (not shown). The sheath 108 is also connected at its other end to the rear end of the hand-held surgical tool body 102, so that the laser energy flux is conveyed from the laser energy source via an optic fiber contained safely within sheath 108 into the surgical tool body 102. In certain sophisticated laser surgical systems, there may also be provided suction or cooling means including elongate tubing 112 connected at one end 114 to suction or cooling devices (not shown) and at another end to the rear end of the surgical tool body 102.

The focus of the present invention is principally on efficient transmission of optic energy, and a more detailed description of the preferred structure follows with particular reference to additional drawing figures.

FIG. 2 illustrates in a partial longitudinal cross-sectional view how an exemplary ray of light may be conveyed from a light-emitting distal end surface 200 of an optic fiber 202 into an optic energy-receiving surface 204 of a first optic element 206 located so that light-emitting surface 200 and light-receiving surface 204 are disposed very close to but not in intimate contact with each other. There may also be an additional optic element 208 cooperating with optic element 206 by being placed in intimate contact therewith at an interface 210.

For present purposes, it is convenient to identify the respective refractive indices of the different materials as follows:

optic fiber 202: $n_f$, intermediate element 206: $n_i$, and optic element 208: $n_o$.

Note that in its passage through the length of optic fiber element 202 the exemplary ray of light will experience "total internal reflection" and be reflected and re-reflected internally within the optic fiber 202. In a straight portion of optic fiber 202 this will occur at an angle $\theta_2$ characterized by the size and material of the optic fiber, as best seen at the lefthand side of FIG. 2. Most light rays will likely be emitted substantially normally with respect to light-emitting end surface 200, but some can be expected to be transmitted like the illustrated exemplary ray. In any case, if there is a physical gap between the light-emitting end surface 200 and the light-receiving surface 204, some of the light transmitted therebetween may be reflected from surface 204, as indicated by the broken arrow-headed line, at an angle $\theta_a$ with respect to a line normal to the surface 204.

In summary, if there is a physical separation between two otherwise parallel surfaces (as indicated in FIG. 2) there will be a loss of some of the optic energy flux at such a gap. The energy thus made unavailable for further transmission through other cooperating optic elements will, in time, heat the zone immediately around the distal end of the optic fiber 202. If a substantial energy flux is being handled, such a loss can become significant and may pose a serious heating problem which may require cooling and add to the expense, complexity, and difficulty of use of the surgical hand-held tool.

FIG. 3 illustrates another situation that can arise, namely one in which the two surfaces across which light is to be transmitted are not parallel even if there are, in fact, held close enough to make actual contact. In a situation like this, a small portion of the light emitted from light-emitting end surface 300 of an optic fiber 302 will be reflected from light-receiving end surface 304 of the contacting optic element 306. In practice, even when care is taken to cut the end of an optic fiber normal to its length, and to intimately contact one optic element to another, situations like that depicted in somewhat exaggerated form in FIG. 3 can arise. This can result in the loss of optic energy flux, thereby reducing the efficiency of optic transmission and, simultaneously, giving rise to local heating problems.

FIG. 4, in the same manner generally as FIG. 2, schematically illustrates the path of an exemplary light ray starting out, for example, as an outermost ray in a parallel beam of light provided from a source (not shown) as a beam of diameter $D_1$. This light beam, indicated by short arrows at the left of FIG. 4, is typically focused by a lens 400 to a light-receiving end surface 402 of an elongate optic fiber element 404. The light ray is internally reflected along optic fiber 404 to be emitted from light-emitting end surface 406 which is ideally held in intimate contact with a light-receiving end surface 408 of an intermediate optic element 410. A light-emitting end surface 412 of intermediate optic element 410 is held in intimate contact with a light-receiving end surface 414 of a second optic element 416.

As generally indicated in FIG. 4, if intimate contact can thus be obtained by adjacent surfaces of cooperating optic light elements, at least the type of losses discussed above with respect to the circumstances schematically illustrated in FIGS. 2 and 3 are avoided. It is the goal of the present invention to facilitate this, even where intimate contact between relatively hard cooperating surfaces of conventional optic elements cannot be readily obtained.

The key to the success of the present invention is in the use of a physically conformable and optically transmissive material for an intermediate optic element like optic element 410 illustrated in FIG. 4. The light-emitting end surface 406 of a relatively fragile and small diameter optic fiber element such as 404 can thus be conveyed efficiently into a typically somewhat larger light-receiving end surface 414 of a conventional optic element 416. This is made possible by the fact that the optically-transmissive material of intermediate element 410 can be made to conform to make intimate contact with each of the two light-transmitting surfaces 406 and 414 simultaneously.

In practical terms, the present invention requires the formation, location, disposition, and use of such a conformable element where efficient and low-loss optical energy transmission is to be effected between adjacent surfaces of two cooperating but not directly contacting optic elements.

A short analytical discussion is provided below to explain the energy loss sought to be avoided and its dependence on the refractive indices of the materials of the cooperating elements.

Referring to FIG. 4, it will be seen that:

$\tan\theta_1 = D_1/2 \cdot L_1$;

$n_1 \cdot \sin\theta_1 = n_2 \cdot \sin\theta_2$ (Snell's Law);

$n_2 \cdot \sin\theta_2 = n_3 \cdot \sin\theta_3$ (Snell's Law)';

$\tan\theta_3 = D_3/2 \cdot L_3$; and $D_3 > 2 \cdot L_3 \cdot \tan\theta_3$.

When a flat-ended optic fiber such as 404 is brought into forcible contact with the conformable material of intermediate element 410, any air initially present therebetween is forced out, and hence Fresnel reflections are minimized. According to Fresnel's law of reflection for unpolarized light at normal incidence, remembering that most of the optical transmission will be at normal incidence and referring to FIG. 4, it will be seen that:

$I_r/I_i = (n_3 - n_2)^2/(n_3 + n_2)^2$, where $I_i$ is the intensity of the incident light and $I_r$ is the intensity of the reflected light at the interface between the optic fiber 404 and conformable element 410.

If the flat light-emitting surface of the optic fiber is not in intimate contact with the light-receiving surface of the adjacent optic element (see FIGS. 2 and 3 for such dispositions), then the percentage of light reflected away from the resulting inadequate interface will be:

$$\begin{aligned}I_r &= I_i \cdot (1.4 - 1.0)^2/(1.4 + 1.0)^2 \\ &= 0.028 I_i \\ &= 2.8\% \text{ of } I_i,\end{aligned}$$

where $n_2 = 1.0$, and $n_3 = 1.4$

However, when the flat end surface of optic fiber is put into intimate contact with the adjacent surface of a cooperating optic element, e.g., by forcible conforming of the material of the latter to obtain an intimate contact/interface at the light-emitting end optic fiber surface as illustrated in FIG. 4, then given $n_4 = 1.54$:

$$\begin{aligned}I_r &= I_i \cdot (1.4 - 1.54)^2/(1.4 + 1.54)^2 \\ &= 0.0023 \, I_i \\ &= 0.23\% \text{ of } I_i, \text{ which is a significant improvement.}\end{aligned}$$

The key, as noted earlier, is that a conformable light-transmissive material is used between the physically hard optic fiber light-transmitting surface 406 and the also hard light-receiving surface 414 of optic element 416.

As best seen in FIG. 5, most of the light-transmission occurs in a direction normal to the interface between light-emitting end surface 406 of optic fiber element 404 and the conformably contacting light-receiving surface 408 of conformable element 410. However, probably due to local stress and/or heating in the conformable material around the edges of the interface, there appears to be a noticeable increase in impedance to transmission of the light flux at the periphery of the interface. This may also have to do with the material properties of the conformable material employed, such materials being discussed more fully hereinbelow.

Further experimentation with an optic fiber having a rounded end showed that such a configuration totally eliminates the localized peripheral impedance to the light flux that was noticed in the flat-ended configuration per FIG. 5. Physically, such impedance in the flat-ended configuration accompanied what appeared to be small bubbles 440 in the conformable material. See FIG. 5.

With the round-ended optic fiber 600, per FIG. 6, the interface between light-emitting surface 602 and the light-receiving surface 604 of conformable element 606 was rounded and free of impedance to the light flux transmitted therethrough. Accordingly, it was concluded that rounding the end of the optic fiber, where it is forcibly held to a conformable element, significantly improves the efficiency of the overall device. Details are now provided of a preferred embodiment, in which this knowledge is applied to advantage in an exemplary laser surgical tool to facilitate the use of replaceable and disposable tip elements.

FIG. 7 illustrates in partial longitudinal cross-sectional view a central portion "P" (see FIG. 1) of the hand-held surgical tool body 102 provided with a number of internal partitions, e.g., 702, 704 and 706. These partitions are each formed with an aperture, namely 708, 710, and 712 respectively, which have centers aligned on a common axis X—X. Note that axis X—X is not an axis of symmetry because of the ergonomically designed but non-symmetrical shape of surgical tool body 102. It is, instead, a reference axis along which the light-emitting end portion of an optic fiber 714 and a tip element assembly 716 are aligned to cooperate with each other.

Between partitions 702 and 704 there is formed an internal generally cylindrical compartment 718 coaxial with axis X—X to slidably contain therein an optic fiber supporting element 720. As best seen FIG. 7, the optic fiber supporting element 720 has a body portion sized to be slidably guided by aperture 708 in partition 702, and a head portion 722 formed adjacent a forward end and sized to be slidably guided by the inside surface of cylindrical compartment 718. Forwardly of head portion 722 there extends an open cylindrical portion 724 formed to have a conical or tapered inside end surface 726.

Optic fiber 714 extends through an axial elongate opening within the optic fiber supporting element 720, and a distal end portion of the optic fiber is potted into place inside the forwardmost cylindrical portion 710 by potting material 728. In this manner, the energy delivering distal end of optic fiber 714, preferably provided with a rounded light-transmitting surface, is held firmly in axial alignment just inside the conical end surface 726.

A compression spring 730 is preferably contained within cylindrical space 718 with one end resting against an inside surface of partition 702 and an opposite end pressing against a rear surface of head portion 722. Spring 730 applies a predetermined bias/force tending to push the light-transmitting curved end surface 732 of optic fiber 714 toward the front end of surgical tool body 102, i.e., rightward in FIG. 7.

Tip element assembly 716 is inserted along axis X—X through a forward opening 734 in the forwardmost portion of surgical tool body 102. This frontal portion is shown in FIG. 7 in phantom lines, including an exemplary O-ring seal 736 disposed to seal around the generally cylindrical elongate outer surface of the tip element assembly 716 to prevent entry of contaminants into the interior space within surgical tool body 102. As will be appreciated, the exact shape, size, and any other control devices contained within surgical tool body 102 in its forwardmost portion are matters of design choice and are not limitations on the present invention. Accordingly, specific details of such aspects of surgical tool body 102 are not necessary to a full understanding of the present invention.

At the forwardmost end of tip element assembly 716 there is provided an energy-applying tip element 738 selected to suit the surgeon's needs. A variety of such tip elements can be designed and utilized, and some are discussed in detail with reference to FIGS. 11–13.

As tip element 716 is inserted through front opening 734 in the surgical tool body 102, it is guided through opening 712 of partition 706 until it contacts a pair of spring clips 740a and 740b, which are shaped, sized and disposed with spring-biased angular portions 742a and 742b to press from opposite sides of tip element assembly 716 toward axis X—X. Spring clips 740a and 740b are preferably made of electrically conductive material, e.g., metal. Close to the inner end of tip element assembly 716 (away from tip element 738) there are provided small radially inward recesses 744a and 744b formed and located to engage with angular portions 742a and 742b of spring clips 740a and 740b respectively to hold tip element assembly 716 in firm and spring-loaded contact with conical surface 726 of optic fiber support body 720. As will be appreciated, the various cooperating and engaging elements are shaped and sized to match one another where they engage.

Tip element assembly 716, as noted, has a body that has a generally cylindrical elongate outer shape. This is obtained by making the body from a metal tube, and adapting it to hold tip element 738 at a forward end and a metal connector element 746 at its rear or inside end. Connector element 746 is formed with an aperture shaped and sized to hold an inside end of an intermediate optic element 748 a forward end of which is to be held in efficient optic communication with tip element 738.

In the preferred embodiment per FIG. 7, note that surgical tool body 102 is provided with a user-operable, preferably spring-biased, switch 106 which is electrically connected via wire 750a to a laser energy power source (not shown). A second wire 750b is connected between switch 106 and spring clip 740b. A third wire 750c is connected between spring clip 740a and a heat fuse 752 mounted on an outside surface of cylindrical portion 724 to be very close to the light-emitting curved surface 732.

A fourth wire 750d connects heat fuse 752 to the laser energy source. The purpose of this wiring connection is to ensure that the laser energy source is turned off, so that no laser energy flux can be emitted from the curved energy-emitting surface of optic fiber 714, unless and until the metal tubing structure of the tip element assembly 738 is in simultaneous contact with both of the electrically conductive spring clips 740a and 740b, heat fuse 752 has not broken electrical continuity and is capable of transmitting electricity therethrough, and switch 106 is being operated. The purpose of heat fuse 752 is to ensure that if there is inefficient optical energy transmission between optic fiber 714 and tip element assembly 738, so that the local temperature therebetween rises to a predetermined safety cut-off level, the fuse material inside fuse 752 will melt and the electrical power supply to the laser power source will be interrupted.

Figure 8:
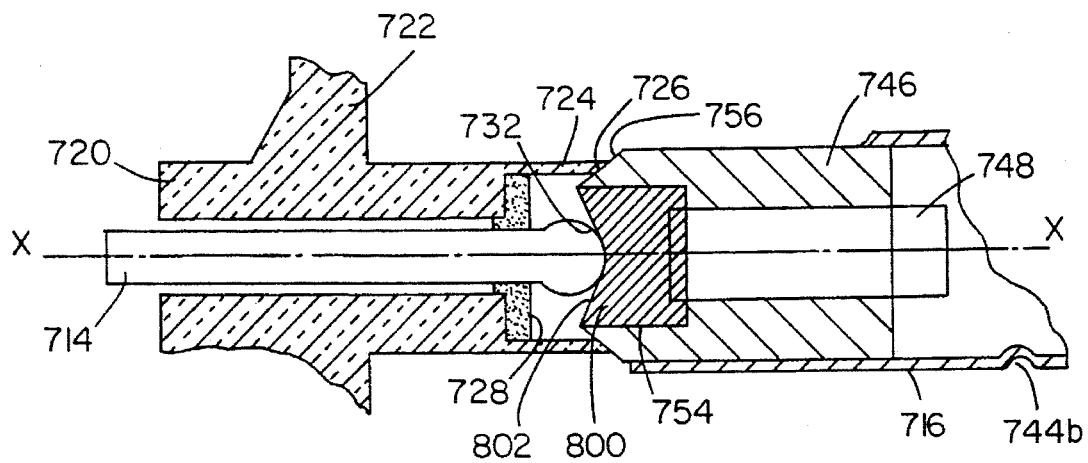
FIG. 8 is a partial axial cross-sectional view to illustrate, in enlarged form, important portions of the structure per FIG. 7.
Figure 9:
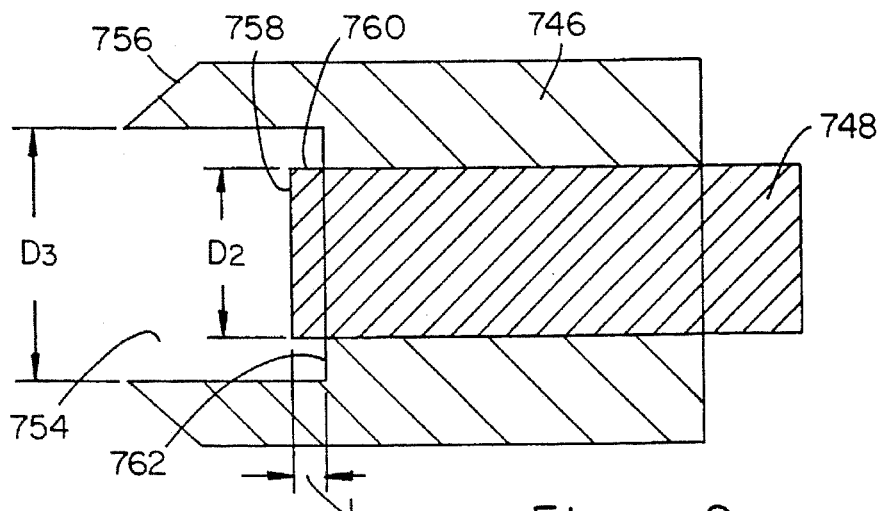
FIG. 9 is a longitudinal cross-sectional view of an end connector provided at a light-receiving end of an optic element and formed to define and accommodate a light-transmissive conformable element in cooperation therewith.
Figure 10:
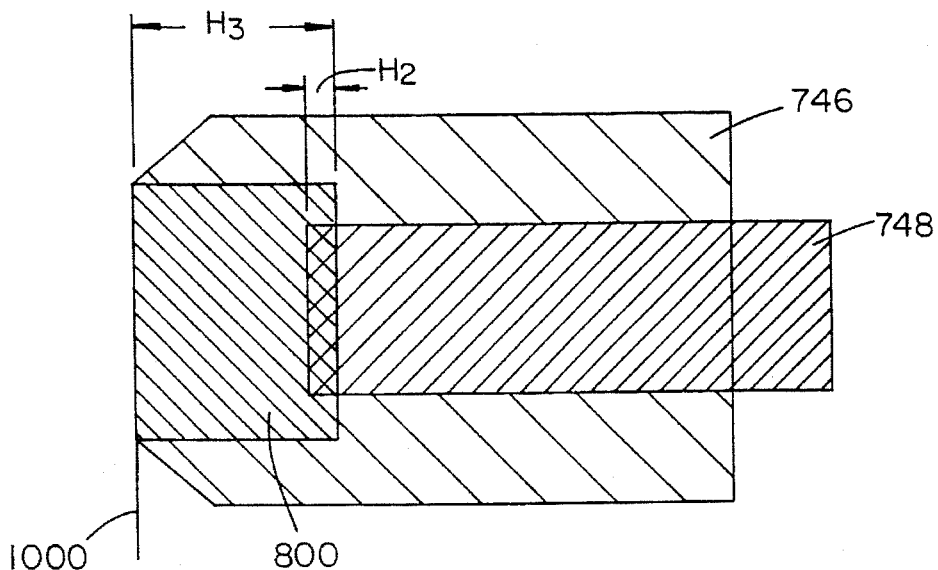
FIG. 10 corresponds to the structure per FIG. 9, and further includes in sectional view a conformable element and a protective sheet covering an end contact surface of the conformable element prior to its use.

Additional details of interest are best understood with reference to FIGS. 8, 9 and 10.

As best seen in FIG. 8, metal connector 746 is fitted around a distal end of intermediate optic element 748 in such a manner that a short length of intermediate optic element 748 projects into an open cylindrical cavity defined in part by a cylindrical surface 754 of diameter larger than that of intermediate optic element 748. This open cylindrical cavity ends at a rim defined by a conical surface 756, the conical angle of which is selected to match the corresponding conical angle of surface 726 of optic fiber support element 720. Therefore, as best seen in FIG. 8, conical surface 726 can be pressed to fit well to conical surface 756.

The space inside cylindrical cavity 754 is filled with a suitable material to form optically transmissive conformable optic element 800 which has an exposed surface 802 conformably pressed to make intimate contact with the curved light-transmitting surface 732 at the end of optic fiber 714.

It should be appreciated that the optic fiber support element 720 is forcibly biased by spring 730 into the above-described conically fitted contact with connector element 746 and that the relevant dimensions of the cooperating parts must be selected so that the curved end surface 732 of optic fiber 714 forcibly presses to the exposed surface 802 of conformable optic element 800 throughout use of the device.

It will also be appreciated that although most of the energy flux transmitted along optic fiber 714 in the arrangement illustrated in FIG. 8 will be directed substantially along axis X—X, a small portion, as exemplified for example by the light ray in FIG. 2, may be directed at an angle to the axis X—X. Then, as indicated in FIG. 2, such a ray will experience internal reflection at the cylindrical side surface of the conformable optic element 206 (in FIG. 2) and 800 (in FIG. 8) in much the same way as a light ray would be internally reflected within a conventional optic fiber such as 202 (in FIG. 2) or 714 (in FIG. 8). If conformable element 800 is formed to totally fill the cylindrical cavity 754, as illustrated in FIG. 8, such internal reflection is greatly facilitated.

Referring now to FIG. 9, there is seen in somewhat enlarged form the geometric relationship between metal connector 746 and the end of intermediate optic element 748 contained therein as described earlier. Note that the diameter "$D_2$" of intermediate optic element 748 is less than the diameter "$D_3$" of cylindrical cavity 754 and that a small length "L" of intermediate optic element 748 projects into cylindrical cavity 754. Accordingly, the space available to be filled with light-transmissive conformable material to form conformable optic element 800 is defined by the end surface 758 and the projecting cylindrical surface 760 of intermediate optic element 748 and the annular bottom surface 762 and the cylindrical surface of cylindrical cavity 754.

There are commercially available, light-transmissive, heat-tolerant, chemically and physically stable, easy-to-pour materials available to form the light-transmissive conformable optic element 800. Typically, such materials come as two-component RTV silicone rubber compounds which are conveniently mixed in small quantities shortly before use. One of the components is the bulk component and the other is a curing agent which causes the bulk component to chemically change to the desired stable form.

Table I, provided below, lists relevant physical characteristics and values for such silicone rubber material available, for example, from the General Electric Corporation.

Very briefly, available from General Electric Corporation are RTV615 and RTV655 silicone rubber compounds which are transparent liquids which with the addition of suitable curing agents cure at room temperature to high strength silicone rubber. These two-component products are commercially supplied with the curing agent in matched kits which are designed for use at a convenience 10:1 ratio by weight. The resulting cured compounds RTV615 and RTV655 are clear and colorless but differ in hardness and low temperature flexibility, both being low viscosity, easily pourable, liquids before curing with nominal viscosities of between 3,000 and 7,000 cps. The RTV655 silicone rubber compound has the capability of remaining flexible, i.e., conformable in the present context, at a temperature approximately 55° C. (100° F.) lower than the RTV615.

Both of these silicone rubber compounds have been used for protection of sensitive electrical components and assemblies against mechanical shock, vibration, moisture, exposure to ozone, ambient dust, assorted chemicals, and other environmental hazards by potting or encapsulation of such components and assemblies.

TABLE I

| | TYPICAL PRODUCT DATA UNCURED PROPERTIES | | | |
| --- | --- | --- | --- | --- |
| | RTV615A | RTV615B | RTV655A | RTV655B |
| Color | Clear, Colorless | Clear, Colorless | Clear, Colorless | Clear, Colorless |
| Consistency | Easily Pourable | Easily Pourable | Easily Pourable | Easily Pourable |
| Viscosity, cps | 4300 | — | 5700 | — |
| Specific Gravity | 1.02 | — | 1.04 | — |

| | UNCURED PROPERTIES WITH CURING AGENT ADDED | |
| --- | --- | --- |
| | RTV615 | RTV655 |
| Color | Clear, Colorless | Clear, Colorless |
| Consistency | Easily Pourable | Easily Pourable |
| Viscosity, cps | 4000 | 5200 |
| Work Time @ 25 C. (77 F.), hrs | 4 | 4 |

| | CURED PROPERTIES (Cured 1 hr. @ 100 C./212 F.) | |
| --- | --- | --- |
| | RTV615 | RTV655 |
| Mechanical | | |
| Hardness, Shore A Durometer | 44 | 45 |
| Tensile Strength, kg/cm$^2$ (psi) | 65 (920) | 65 (920) |

TABLE I-continued

| | | |
|---|---|---|
| Elongation, % | 160 | 120 |
| Shrinkage, % | 0.2 | 0.2 |
| Refractive Index | 1.406 | 1.430 |
| Electrical | | |
| Dielectric Strength, kv/mm (v/mil) (1.9 mm thick) | 20.5 (520) | 20.9 (530) |
| Dielectric Constant @ 1000 Hz | 2.7 | 2.69 |
| Dissipation Factor @ 1000 Hz | 0.0006 | 0.0004 |
| Volume Resistivity, ohm-cm | $3.2 \times 10^{15}$ | $1.2 \times 10^{15}$ |
| Thermal | | |
| Useful Temperature Range, °C. (°F.) | −60 to 204 (−75 to 400) | −115 to 204 (−175 to 400) |
| Thermal Conductivity, gm-cal/sec, cm², °C./cm (Btu/hr, ft², °F./ft) | 0.00045 (0.11) | 0.00045 (0.11) |
| Coefficient of Expansion, cm/cm, °C. (in/in, °F.) | $27 \times 10^{-5}$ ($15.3 \times 10^{-5}$) | $33 \times 10^{-5}$ ($18.3 \times 10^{-5}$) |
| Specific Heat, cal/gm, °C. (Btu/lb, °F.) | 0.3 (0.3) | 0.3 (0.3) |

Both silicone rubber compounds have optical clarity believed to be sufficient for a variety of light-transmitting applications, e.g., potting solar cells for maximum light transmission. Both compounds retain their elastomeric properties at temperatures up to 204° C. (400° F.).

Also available commercially is a range of automatic equipment designed to meter, mix, deaerate, and dispense such two-component RTV silicone rubber compounds. For small batches, it may sufficient to mix a suitable quantity of the silicone rubber material and, with a conventional hypodermic device, to place sufficient material within cylindrical cavity 754 to just fill that cavity. Since the silicone rubber material will cure at room temperature, it is also desirable to cover the material by the placement of a thin, protective sheet, e.g., a small piece of nonstick plastic or paper 1000, as indicated in FIG. 10. The protective sheet can be readily removed by peeling it off immediately prior to insertion of the tip element assembly 716 into the surgical tool body 102 for clipped-in disposition for use.

As will be readily appreciated, from knowledge of dimensions such as diameters "$D_2$" and "$D_3$" as well as heights "$H_2$" and "$H_3$" (as best seen in FIG. 10) persons of ordinary skill in the art can easily employ the previously-referenced commercially available equipment to meter precise quantities of mixed silicone rubber compound and curing agent to create, in place for use, light-transmissive conformable optic element 800. Obviously, with the application of other known techniques, the entire process can be integrated into a manufacturing facility.

It should be apparent that intermediate optic element 748 can be one which has an extended length and an extreme distal end portion projecting outwardly of surgical tool body 102 as indicated generally in FIG. 1. It can be formed so that no additional elements would be needed between the interface formed by intimate contact between conformable element 800 and the rounded end of optical fiber 714 and a tip surface from which laser energy flux is either emitted or at which it is used to locally heat a surface for surgical applications. An obvious alternative would be to make intermediate optic element 748 such as to have a second metal connector like metal connector 746 with a corresponding light-transmissive conformable optic element formed therein, the latter being optically coupled to a separate tip element by which laser energy is to be applied for use. Since the logic of this is clearly apparent from the above description of the present invention, further discussion of such structural details is not believed to be necessary for persons of ordinary skill in the art to practice such a variation of the present invention. In its simplest form, such an arrangement would employ a laser tip element biased to press to the second conformable element formed at a forward end of the intermediate optic element.

The advantages of the above-described structure should now be apparent. An elongate optic fiber, properly sheathed as indicated in FIG. 1, can be used to connect a surgical tool body 102 to a laser source. The laser source would not be in a position to transmit a laser energy flux until and unless a replaceable or disposable tip element assembly is properly inserted to its clipped-in state so that the necessary electrical connections are made and available as described earlier. Even then, laser energy flux would reach the tip element end only when the surgeon presses switch 106. Following sufficient use of the tip element/tip element assembly, the surgeon can simply pull it out of the surgical tool body 102 to overcome the retaining force of spring clips 740a and 740b, remove the protective cover sheet 1000 from the tip element assembly and insert the latter into opening 734 of surgical tool body 102. This can be accomplished in only a few seconds and would enable the surgeon to continue the operation without significant distraction, selectively using a variety of laser energy application tips or simply replacing a contaminated or deteriorated tip element.

There are, as mentioned earlier, other broader applications possible, e.g., the tip element may be part of an observation or sensing system exposed to radioactivity or erosion. In each case, a new tip element can be used easily to replace a used one.

Figure 11:
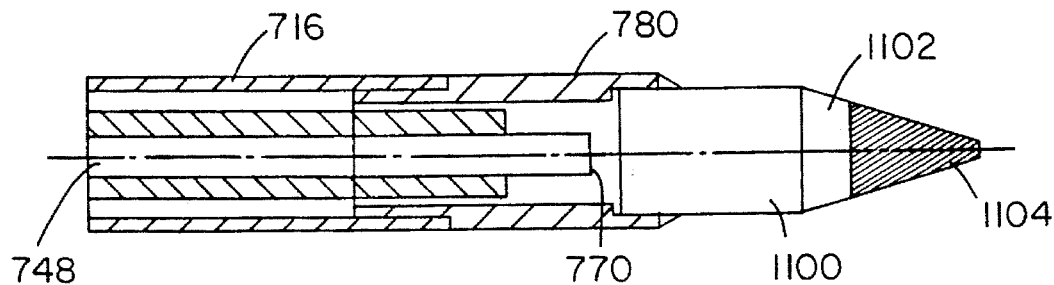
FIGS. 11, 12, and 13 illustrate in respective axial cross-sectional views structural details of three types of replaceable laser surgical tip elements usable with the preferred embodiment of this invention.
Figure 12:
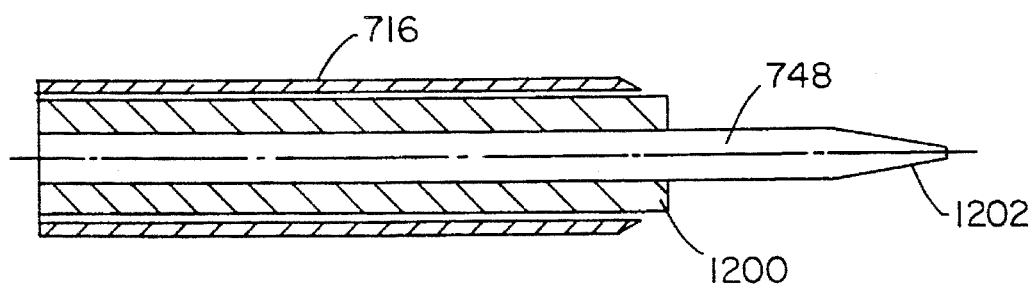
Figure 13:
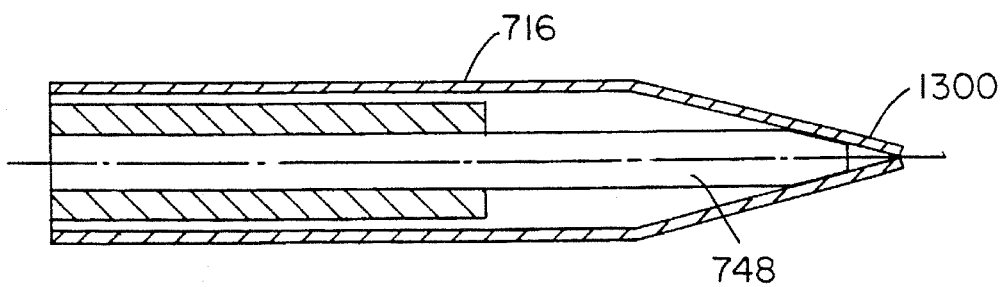

As noted earlier, the actual application of laser energy is effected through the extreme tip portion of the tip element assembly. FIGS. 11, 12 and 13 illustrate in partially-sectioned longitudinal views three exemplary forms for such a tip element structure.

In the structure per FIG. 11, referring back to FIG. 7 for commonly numbered elements, optic element 748 has a distal end (i.e., one opposite to an end in direct contact with conformable optic element 800) with a flat energy-emitting end surface 770. The corresponding distal end of the cylindrical tube forming the body of tip element assembly 716 is fitted to a tip element connector 780 (see FIG. 11) into a forward end of which is located an optically transmissive tip element 1100 which has a conical forward end 1102.

For applications in which laser light energy is not to be emitted directly to irradiate tissue, but is to be utilized only to heat a surface of the tip element for contact application to cause cauterization or coagulation of body fluids, a thin opaque surface region 1104 is formed to absorb all the energy flux received thereat. In this manner, by operation of switch 106, the surgeon can cause a flux of laser energy to traverse from the laser source through optic fiber 714, through conformable optic element 800, through optic element 748 and through the body of tip element 1100 to surface region 1104 where the laser energy flux is totally converted to heat. Such a surface region suffers significant thermal cycling. If it is provided by the application of a mechanically-adhered laser-energy absorbing metal or the like, such a surface region may experience delamination and deterioration.

A preferred structural form for such a surface region and a method for forming the same is one obtained as disclosed in copending U.S. patent application Ser. No. 07/723,987, filed on Jul. 1, 1991, which is hereby expressly incorporated by reference. The surface region produced as taught in the incorporated material is highly efficient in absorbing laser energy flux and converting it to heat at the surface of tip element and is free of the dangers of rapid deterioration, delamination and the like.

FIG. 12 illustrates a somewhat simpler distal end structure for delivering laser energy conveyed across light-transmissive conformable element 800. In this structure, a sheath 1200 may be shaped and sized to locate optic element 748 coaxially within the forwardmost end of tip element assembly 716. Optic element 748 may itself be provided with a shaped tip, e.g., a conical or knife-blade type shape identified generally as 1202 in FIG. 12. With such a structure, laser energy flux conveyed across optically-transmissive conformable element 800 would be efficiently transmitted into and along optic element 748 and emitted from its energy-delivery portion 1202. A laser energy absorbing region may be provided to some or part of optic element 748 along the lines discussed with reference to FIG. 11 above.

FIG. 13 illustrates a structure in which the steel metal tube body of tip element 716 is swaged at its distal forward end to have a conical form to the inside surface of which is fitted the conical end of optic element 748. A sheath 1300 may be provided to support and coaxially locate optic element 748 inside tip element assembly 716. With this arrangement, laser energy transmitted across conformable element 800 would be received within optic element 748, travel along its length, and then reach the inside surface of the conical metal wall of the forwardmost portion 1300 of metal tubing to be absorbed and converted to heat thereat. Such a tip element could be utilized in the same manner as the tip element illustrated in FIG. 11, i.e., the heated external surface may be applied to effect cauterization or coagulation of body fluids.

Numerous other variations will no doubt occur to persons of ordinary skill in the art. The key advantage according to this invention would be the same in each case, that laser light energy emitted from a light-emitting surface of a long-use optic fiber connected to a laser light source is efficiently transmitted into an optic element by the interposition therebetween of a light-transmissive conformable element to reduce Fresnel losses. This reduces the need for cooling, may prolong the useful life of the surgical tool body, and significantly facilitates the rapid changing of the tip element assembly by simple insertion of a replacement into the surgical tool body.

To protect against accidents that may be caused by the ingress of moisture or other electrically conducting material between spring clips 740*a* and 740*b* when a tip element assembly is not inserted between the clips, it may be advisable to insert a plastic spacer having the same external shape and size as a regular metal-bodied tip element assembly. The insertion of such a protective "dummy" non-conductive plastic element between the clips 740*a* and 740*b* will thus ensure that no external dirt can enter the surgical tool body 102 from its forwardmost opening and, at the same time, ensure that electrical communication between spring clips 740*a* and 740*b* cannot take place. With this arrangement, even if the surgeon accidentally presses switch 106, power will not be provided to the laser energy source and inadvertent radiation with laser energy will be avoided.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A system for providing efficient optical communication between a first optic element and a second optic element, comprising:

an optically transmissive preformed conformable element disposed between the first and second optic elements for simultaneously and conformably contacting both an optic energy-emitting surface of the first element and an optic energy-receiving surface of the second element, to thereby provide an optic path therebetween; and biasing means for forcibly maintaining said conformable element in said simultaneous contact with said first and second optic elements, wherein the optic energy-emitting surface of the first optic element is rounded and is forcibly biased by said biasing means toward said conformable element to conform a corresponding surface thereof into conforming contact with said rounded surface of said first optic element.

2. The system according to claim 1, further comprising:

safety means for interrupting a flow of optic energy between the first optic element and the second optic element in response to a rise in local temperature to a predetermined safety cut-off level where the first optic element contacts the conformable element.

3. The system according to claim 2, wherein:

said safety means comprises a temperature-responsive fuse electrically connected to a source providing said optic energy to the first optic element.

4. The system according to claim 3, further comprising:

holding means for holding said second optic element relative to said first optic element with said conformable element disposed therebetween, said holding means comprising an electrically conducting element which is required to complete an electrical current path through said fuse.

5. A system for enabling efficient transmission of an optic energy flux between a first optic element and a second optic element when the first and second optic elements are held in a non-contacting but cooperative relationship with respect to one another to provide portions of a common optic path to the optic energy flux, comprising:

an element holding means for holding an optic energy-emitting surface of the first optic element in a predetermined disposition with respect to an optic energy-receiving surface of the second optic element;

optically transmissive conformable means disposed intermediate the first and second optic elements so as to make simultaneous conforming optical contact at an exposed energy-receiving conformable surface with the optical energy-emitting surface of the first optic element and at another energy-transmitting conformable surface with the optic energy-receiving surface of the second optic element, to thereby provide an efficient optic path to the optic energy flux between said first and second optic elements; and means for biasing the first optic element with respect to the optically transmissive conformable means to press the energy-emitting surface of the first optic element to the optically transmissive conformable means to obtain said conforming contact between the optic energy-emitting surface of the first optic element and the exposed energy-receiving conformable surface of the optically transmissive conformable means, wherein said element holding means comprises a containment space defined in part by the energy-receiving surface of the second optic element, and said optically transmissive conformable means comprises a quantity of an optically transmissive conformable material held in said containment space in conforming contact with the optic energy-receiving surface of the second optic element, said optically transmissive conformable material being shaped to be forcibly held by said element holding means so that the exposed energy-receiving conformable surface is held in conforming contact with the energy-emitting surface of the first optic element.

6. The system according to claim 5, wherein:

said optically transmissive conformable material comprises a silicone rubber.

7. The system according to claim 5, wherein:

said second optic element comprises an optic energy-delivering surface at which optic energy received via the optically transmissive conformable means is delivered for use.

8. The system according to claim 7, wherein:

means for biasing the first optic element with respect to the optically transmissive conformable means, disposed in the element holding means so as to press the energy-emitting surface of the first optic element to the optically transmissive conformable means to obtain said conforming contact between the optic energy-emitting surface of the first optic element and the optically transmissive conformable means.

9. The system according to claim 5, further comprising:

means for controlling the optic energy flux and for preventing the optical energy flux whenever the conformable means ceases said simultaneous contact with said first and second optic elements.

10. The system according to claim 9, further comprising:

means for sensing a temperature adjacent the optic energy-emitting surface of the first optic element and for stopping said optic energy flux when a predetermined temperature is sensed.

11. The system according to claim 9, wherein:

said second optic element comprises a surface portion for absorbing said optic energy flux and converting the absorbed optic energy to heat.

12. A system for enabling efficient transmission of an optical energy flux from an optic energy-emitting surface of a first optic element into an optic energy-receiving surface of a detachable second optic element, comprising:

first means for holding the first optic element with the optic energy-emitting surface thereof biased in a predetermined orientation;

an optically transmissive conformable element having an optic energy receiving conformable surface and an optic energy emitting conformable surface with an optic path therebetween;

second means for holding said optically transmissive conformable element with the optic energy emitting conformable surface thereof in conforming contact with the optic energy-receiving surface of the second optic element; and third means for detachably holding the second optic element so that the optic energy receiving conformable surface of said optically transmissive conformable element is forced into conforming contact with the energy-emitting surface of the first optic element.

13. The system according to claim 12, wherein:

the first means comprises a hollow handle defining an interior space containing resilient biasing means supporting a distal end of the first optic element so that the optic energy-emitting surface of the first optic element is biased in said predetermined orientation to ensure that the optic energy-emitting surface is forcibly contacted by the optic energy receiving conformable surface of the optically transmissive conformable element, whereafter the resilient biasing means maintains said biased conforming contact between the optic energy-emitting surface and the optically transmissive conformable element.

14. The system according to claim 13, further comprising:

engagement means disposed within said interior space for releasably engaging with the second optic element so that the optically transmissive conformable element is releasably held in said conforming contact with the optical energy-emitting surface of the first optic element.

15. The system according to claim 14, wherein:

the first element comprises an optic fiber connected to an optic energy source to receive the optic energy flux and convey the received optic energy flux to a distal end comprising said energy-emitting surface;

the second optic element comprises an engageable outer housing and a connecter at a distal end of the second optic element, said connector being formed to surround the optic energy-receiving surface of the second optic element and to hold the optically transmissive conformable element thereto; and the engagement means is mounted within said handle to releasably engage with said engageable outer sleeve.

16. The system according to claim 15, wherein:

said third means comprises electrically conducting means for terminating said optic energy flux whenever said optically transmissive conformable element ceases to make said conforming contact with the energy-emitting surface of the first optic element.

17. A system for enabling efficient transmission of an optical energy flux from an optic energy-emitting surface of a first optic element into an optic energy-receiving surface of a detachable second optic element, comprising:

first means for holding the first optic element with the optic energy-emitting surface thereof biased in a predetermined orientation;

second means for holding an optically transmissive conformable element in conforming contact with the optic energy-receiving surface of the second optic element; and third means for detachably holding the second optic element so that the optically transmissive conformable element is forced into conforming contact with the energy-emitting surface of the first optic element, wherein the first means comprises a hollow handle defining an interior space containing resilient biasing means supporting a distal end of the first optic element so that the optic energy-emitting surface of the first optic element is biased in said predetermined orientation thereof to ensure that the optic energy-emitting surface is contacted by the optically transmissive conformable element, whereafter the resilient biasing means maintains conforming contact between the optic energy-emitting surface and the optically transmissive conformable element, engagement means disposed within said interior space for releasably engaging with the second optic element so that the optically transmissive conformable element is releasably held in said conforming contact with the optical energy-emitting surface of the first optic element, the first element comprises an optic fiber connected to an optic energy source to receive the optic energy flux and convey the received optic energy flux to a distal end comprising said energy-emitting surface, the second optic element comprises an engageable outer housing and a connector at a distal end of the second optic element, said connector being formed to surround the optic energy-receiving surface of the second optic element and to hold the optically transmissive conformable element thereof, the engagement means is mounted within said handle to releasably engage with said engageable outer sleeve, said third means comprises electrically conducting means for terminating said optic energy flux whenever said optically transmissive conformable element ceases to make said conforming contact with the energy-emitting surface of the first optic element, and the third means comprises fuse means for interrupting electrical continuity upon being actuated at a predetermined temperature.

18. A method for enabling efficient optical communication between a first optic element having an optic energy-emitting surface in a predetermined disposition with respect to an optic energy-receiving surface of a second optic element, comprising the step of:

preforming an optically transmissive conformable element having an optic energy-receiving conformable surface and an optic energy emitting conformable surface in contact with said optic energy-emitting surface of the first element;

placing the optic energy-emitting surface of the preformed optically transmissive conformable element in contact with said optic energy-receiving surface of the second optic element to thereby provide an optical path between the first and second optic elements; and applying a biasing force to bias said optic energy-emitting surface of the first optic element toward said optically transmissive conformable element to maintain said conforming contact therebetween.

19. A method for enabling efficient transmission of an optic energy flux between a first optic element and a second optic element, comprising the steps of:

holding said first and second optic elements in a non-contacting but cooperative relationship with respect to one another to provide respective first and second portions of a common optic path to the optic energy flux emitted from an optic energy-emitting surface of the first element and received by an optic energy-receiving surface of the second element;

disposing a preformed optically transmissive conformable element intermediate the first and second optic elements; and biasing the first optic element relative to the second optic element so as to conform the optically transmissive conformable element into making simultaneous and efficient optical contact at a conformable energy receiving surface with the optical energy-emitting surface of the first optic element and at a conformable energy emitting surface with the optic energy-receiving surface of the second element, to thereby provide a corresponding portion of said optic path to the optic energy flux between said first and second optic elements.

20. The method according to claim 19, comprising the further step of:

providing a safety fuse adjacent to the optic energy-emitting surface of the first optic element biased in conforming contact with the conformable element so that the safety fuse will act to interrupt further flow of optic energy when a predetermined high temperature is reached due to inefficient transfer of optic energy thereat.

21. A method for enabling efficient optical communication between a first optic element having an optic energy-emitting surface in a predetermined disposition with respect to an optic energy-receiving surface of a second optic element, comprising the step of:

providing a preformed optically transmissive conformable element having an optic energy-receiving conformable surface and an optic energy emitting conformable surface in respective simultaneous and conforming contact thereat with said optic energy-emitting surface of the first element and said optic energy-receiving surface of the second optic element to thereby provide an optical path therebetween;

applying a biasing force to bias said optic energy-emitting surface of the first optic element toward said optically transmissive conformable element to maintain said conforming contact therebetween; and providing a safety fuse adjacent to the optic energy-emitting surface of the first optic element biased in conforming contact with the conformable element so that the safety fuse will act to interrupt further flow of optic energy when a predetermined high temperature is reached due to inefficient transfer of optic energy thereat.

* * * * *